United States Patent [19]

Dhingra et al.

[11] 4,087,278
[45] May 2, 1978

[54] HERBICIDAL CHLORAL HYDRATE BIS-ESTER OF 2,2,3-TRICHLOROPROPIONIC ACID

[75] Inventors: Yog R. Dhingra; Zdravko Jezic, both of Midland, Mich.

[73] Assignee: The Dow Chemical Company, Midland, Mich.

[21] Appl. No.: 502,709

[22] Filed: Sep. 3, 1974

Related U.S. Application Data

[62] Division of Ser. No. 343,717, Mar. 21, 1973, Pat. No. 3,882,170.

[51] Int. Cl.$^2$ ............................................. A01N 9/24
[52] U.S. Cl. .................................................. 71/106
[58] Field of Search ................................. 71/106, 122

[56] References Cited

U.S. PATENT DOCUMENTS

| | | | |
|---|---|---|---|
| 2,807,530 | 9/1957 | Barrons | 71/113 |
| 2,821,546 | 1/1958 | Senkbeil et al. | 71/106 X |
| 2,889,358 | 6/1959 | Guest et al. | 71/106 X |
| 2,889,359 | 6/1969 | Guest et al. | 71/106 X |

OTHER PUBLICATIONS

Kochmann et al. Chem. Abst. vol. 74 (1971) 22059f.

*Primary Examiner*—Lewis Gotts
*Assistant Examiner*—Catherine L. Mills
*Attorney, Agent, or Firm*—Theodore Post; D. L. DeJoseph

[57] ABSTRACT

Chloral hydrate bis-ester of 2,2,3-trichloropropionic acid, $CCl_3CH(OCOCCl_2CH_2Cl)_2$, its preparation by reacting chloral hydrate with 2,2,3-trichloropropionyl chloride and herbicidal compositions containing chloral hydrate bis-ester of 2,2,3-trichloropropionic acid.

2 Claims, No Drawings

HERBICIDAL CHLORAL HYDRATE BIS-ESTER OF 2,2,3-TRICHLOROPROPIONIC ACID

This is a division of application Ser. No. 343,717, filed Mar. 21, 1973, now U.S. Pat. No. 3,882,170.

BACKGROUND OF THE INVENTION

It is known that 2,2-dichloropropionic acid as such and in a salt form is a herbicide; U.S. Pat. No. 2,642,354. It is also known that 2,2,3-trichloropropionic acid as such and in a salt form is effective as a herbicide; U.S. Pat. No. 2,807,530. Both the free acids and salts of these compounds are highly corrosive, relatively volatile and difficult to formulate as stable, non-corrosive liquid compositions. They are therefore usually used in solid particulate form, with or without a particulate solid carrier.

SUMMARY OF THE INVENTION

The present invention concerns the chloral hydrate bis-ester of 2,2,3-trichloropropionic acid, $CCl_3CH(OCOCCl_2CH_2Cl)_2$, its method of preparation and herbicidal compositions containing the same. The compound will hereinafter be referred to as "Compound".

The Compound is advantageously prepared by reacting chloral hydrate with 2,2,3-trichloropropionyl chloride in an inert organic solvent at a hydrogen chloride byproduct liberating temperature, advantageously between about room temperature and about reflux temperature of the solvent reaction medium and preferably between about 40° C. and about 75° C. until reaction is substantially complete. The reaction is completed when hydrogen chloride ceases to be evolved. However, it is preferable to carry out the reaction in the presence of an acid acceptor, such as, for example, pyridine, trimethylamine, triethylamine, and the like. Since the reactants react in proportions of two moles of acid chloride to one mole of chloral hydrate, such proportions are preferred. Also, to bind the evolved hydrogen chloride, a 2-molar proportion or a small excess over a 2-molar proportion of an acid acceptor is advantageously used. The reaction is normally completed within about 1½ to 2 hours. The reaction product is recovered in usual ways, i.e., for example, by filtering off the hydrochloride byproduct from the cooled reaction mixture, washing the reaction mixture with aqueous 5% sodium carbonate or equivalent base and with water, drying the resulting solution and removing the solvent in vacuo to give the Compound.

In practice, a solution of a 1-molar proportion of chloral hydrate and about a 2.2-molar proportion of the acid acceptor in a dry inert organic solvent as reaction medium is warmed to reaction temperature with stirring and to it is gradually added a 2-molar proportion of the acid chloride. The reaction mixture is maintained at reaction temperature with stirring for about 90 minutes. The reaction mixture is cooled, filtered to remove amine hydrochloride, the resulting solution washed with aqueous 5% sodium carbonate or equivalent base then with water and subsequently dried. The solvent is removed in vacuo to leave crude product and the residue is distilled under vacuum to give the Compound.

The following exemplary materials further describe the invention and the manner and process of making and using it to enable the art skilled to make and use the same and set forth the best mode contemplated by the inventors of carrying out the invention.

EXAMPLE 1

Preparation of chloral hydrate bis ester of 2,2,3-trichloropropionic acid

A solution of 17.4 g. (0.105 mole) chloral hydrate and 17 g. (0.21 mole) pyridine in 100 ml. dry benzene was placed in a 3-necked flask equipped with magnetic stirrer, condenser, thermometer and dropping funnel. The solution was warmed to 50°-60° C. and 41.5 g. (0.21 mole) of 2,2,3-trichloropropionyl chloride was added dropwise with stirring. The solution was heated to 70° C. and maintained there for 90 minutes. The reaction mixture was cooled and filtered to remove pyridine hydrochloride. The benzene solution was washed with aqueous 5% sodium carbonate solution, then twice with water and subsequently dried. The solvent was removed in vacuo. The residue was distilled under vacuum to give the titular product, b.p. 157°-160° C./1.2 mm Hg.

The Compound is a viscous high boiling liquid. It is much less corrosive than trichloroacetic acid, 2,2-dichloropropionic acid and their salts. It is stable as an ester against breakdown in storage. It does not need to be dried prior to use or formulation. It is readily soluble in agricultural spray oils and petroleum distillates such as, for example, diesel fuel, kerosene, fuel oil, naphthas and Stoddard solvent; and since it is a liquid, it lends itself readily to liquid formulations and concentrates and especially oil-in-water emulsion formulations.

According to the present invention, it has been discovered that the growth of plants may be suppressed by the action of the Compound. More particularly, it has been discovered that the growth of germinant seeds may be controlled by exposing the seeds to the action of a growth-inhibiting amount of the Compound. Further, the Compound has a high degree of persistency in soil and gives excellent controls of many undesirable plant species for periods ranging up to several months.

The exposure of seeds to the action of the Compound gives rise to varying degrees of response in germinant seeds depending upon the seed and the dosage of the Compound employed. When very large dosages are dispersed in growth media, a persistent inhibition of the growth of seeds is obtained. This approaches a sterilizing action. The weathering action of the sun, rain and possibly the decomposition of the Compound by the action of bacteria eventually frees the growth media of the toxicant. Prior thereto, the Compound gradually hydrolyzes to give two moles of 2,2,3-trichloropropionic acid and one mole of chloral hydrate per mole of the Compound. The chloral hydrate oxidizes in the soil to give trichloroacetic acid. Consequently, on a weight basis, 2 pounds of the Compound is as effective as a growth suppressant as 3 pounds of trichloroacetic acid and more effective because less volatile and more stable than an equivalent amount of 2,2,3-trichloropropionic acid. Soil applications of more dilute dosages suppress the growth of the seeds of many broadleaf and narrowleaf weed species while having little or no effect upon stands of grasses such as blue grass and creeping red fescue. Thus, it is possible to effect a selective control of many undesirable weeds in established grasses of these species.

The exposure of the seeds to the action of a growth-inhibiting amount of the Compound is essential for the practice of the present invention. The exact dosage to be employed to obtain such exposure is dependent upon such factors as soil type, depth to which the Compound is distributed in the soil and the amount of rainfall, as well as upon the plant species to be controlled. Good results are obtained when the germinant seeds are exposed to dosages of Compound of from 4 to 150 pounds or more of the acid equivalent of a mixture of 2-molar proportions of 2,2,3-trichloropropionic acid and one-molar proportion of trichloroacetic acid per acre.

Methods and compositions employing the oil-soluble Compound comprise a preferred embodiment of the present invention. The method of the present invention may be carried out by distributing the unmodified Compound in growth media. However, the present method also embraces the employment of liquid, dust or granular compositions containing the Compound. In such usage, the toxicant Compound may be modified with one or a plurality of additaments or herbicide adjuvants, including water or other liquid carriers, surface active dispersing agents and finely divided inert solids. Depending upon the concentration of toxicant, such augmented compositions are adapted to be distributed in soil or to be employed as concentrates and subsequently diluted with additional inert carrier to produce the ultimate treating compositions.

The exact concentration of the Compound to be employed in the treating compositions is not critical and may vary considerably provided the required dosage of effective agent is supplied in the growth medium. The concentration of Compound in liquid compositions employed to supply the desired dosage generally is from about 0.01 to 50 percent by weight, although concentrations as high as 90 percent by weight are sometimes employed. In dusts or granules, the concentration of the Compound may be from about 0.1 to 20 percent by weight. In compositions to be employed as concentrates, the Compound may be present in a concentration of from 5 to 95 percent by weight.

The quantity of treating composition to be applied may vary considerably provided that the required dosage of Compound is applied in sufficient of the finished composition to facilitate the penetration and distribution of said Compound in growth media. The required amount of the Compound in the soil conveniently may be supplied per acre treated in from 10 to 27,000 gallons or more of the liquid carrier or in from 50 to 2,000 pounds of the inert solid carrier. In the application of dusts, good results are obtained with from 40 to 200 pounds of finished dust per acre, the only requirement being that the required toxicant dosage be supplied in sufficient dust to achieve good coverage of the growth media.

Liquid compositions containing the desired amount of Compound may be prepared by dispersing the Compound in an organic liquid, with or without the aid of a suitable surface-active dispersing agent such as an ionic or non-ionic emulsifying agent. Suitable organic liquid carriers include the agricultural spray oils and the petroleum distillates such as diesel fuel, kerosene, fuel oil, naphthas and Stoddard solvent. Among the latter, the petroleum distillates are generally preferred. The organic liquid compositions may contain an external water phase as a diluent carrier for the toxicant ingredient. Such compositions comprise an oil-in-water emulsion, i.e., a mixture of water, emulsifying agent and organic liquid. In the liquid compositions, the choice of dispersing and emulsifying agent and the amount thereof employed is dictated by the nature of the composition and by the ability of the agent to facilitate the dispersion of the Compound in the carrier to produce the desired composition. Dispersing and emulsifying agents which may be employed in the compositions include the condensation products of alkylene oxides with phenols and organic acids, alkyl aryl sulfonates, polyoxyalkylene derivatives of sorbitan esters, complex ether alcohols, mahogany soaps and the like.

In the preparation of dust compositions, the Compound is dispersed in and on a finely divided inert solid such as clay, talc, chalk, gypsum and the like. In such operations, the finely divided carrier is mechanically mixed with the Compound. Similarly, dust compositions containing the Compound may be prepared from various of the solid surface active dispersing agents such as bentonite, fuller's earth, attapulgite and other clays. Depending upon the proportion of ingredients, these dust compositions may be employed as concentrates and subsequently diluted with additional solid surface active dispersing agent or with chalk, talc or gypsum and the like to obtain the desired amount of Compound in a composition adapted to be employed for the suppression of the growth of plants. Also, such dust compositions may be dispersed in water, with or without the aid of a dispersing agent, to form spray mixtures.

When operating in accordance with the present invention, growth inhibiting amounts of Compound are dispersed in soil or growth media in any convenient fashion. Applications to growth media may be carried out by simply mixing with the media, sometimes in admixture with fertilizer, by application to the surface of soil and thereafter dragging or discing into the soil to the desired depth, or by employing a liquid carrier to accomplish the penetration and impregnation. The application of spray and dust compositions to the surface of soil may be carried out by conventional methods, e.g., power dusters, boom and hand sprayers and spray dusters.

In a further method, the distribution of the Compound in soil may be accomplished by introducing the Compound by dispersing it or emulsifying it in the water employed to irrigate the soil. In such procedures, the amount of water may be varied with the porosity and water holding capacity of the soil to obtain a desired depth of distribution of the Compound.

Consequently, the inventive methods and compositions are useful in soil incorporation for perennial grass control; for selective annual grass control in beet, rape, potato, pea, flax and sunflower crops; and for a chemical summer fallow.

The following example is illustrative of the inventive method of use but is not to be construed as limiting:

EXAMPLE 2

Pre-emergence herbicide test

Five by 10 by 2 inch pots were filled to within one inch of the top with a medium-textured soil and seeds of Johnson grass, barnyard grass, foxtail, wild oats and crabgrass were sown in their appropriate area. The seeds were then covered with a ½ inch layer of a sandy soil and Compound formulated as an oil-in-water emulsion was drenched onto the soil surface in sufficient volume to wet the top 1½ to 2 inches of soil at a concentration of 2 lb./acre. The pots were maintained in a greenhouse and were top-watered as necessary. Final readings were made about two weeks after treatment, the exact time depending upon the rate of plant growth.

Readings were based on the germination and the growth of treated plants compared with that of untreated plants. Readings of 0 = no visible effects and 100 = all plants dead. Observations were also made on the type of injury, such as malformation and stunting. Readings and observations noted for various plant responses are given below.

Table

| Seeds | Reading | Observations |
|---|---|---|
| Johnson grass | 70 | stunted |
| barnyard grass | 50 | stunted, malformed |
| foxtail | 70 | stunted, stand reduction |
| wild oats | 80 | stunted, malformed |
| crabgrass | 80 | stunted, malformed |

A reading of 50 or higher with stunting of the seedlings indicates that the seedlings will not recover adequately to become conpetitive in a vigorous crop.

The herbicidal formulation used in this example was prepared by dissolving 25 parts by weight of Compound in 70 parts by weight of xylene containing 5 parts by weight of Triton X-155 nonionic alkaryl polyether alcohol emulsifier to form a concentrate and adding the concentrate to water with mixing to provide a dispersion in water containing about 0.5 lb. of Compound per 100 gal. of aqueous dispersion.

What is claimed is:

1. A process for controlling plants which comprises contacting plant seeds by impregnating soil containing their seeds with a seed growth-inhibiting amount of the chloral hydrate bis-ester of 2,2,3-trichloropropionic acid.

2. A herbicide composition which comprises a carrier and a herbicidal concentration of the chloral hydrate bis-ester of 2,2,3-trichloropropionic acid.

* * * * *

UNITED STATES PATENT AND TRADEMARK OFFICE
CERTIFICATE OF CORRECTION

PATENT NO. : 4,087,278
DATED : May 2, 1978
INVENTOR(S) : Yog R. Dhingra and Zdravko Jezic It is certified that error appears in the above—identified patent and that said Letters Patent are hereby corrected as shown below:

Title Page under "References Cited", fourth reference
"2,889,359    6/1969"    should read --2,889,359   6/1959--;

Signed and Sealed this

Tenth Day of October 1978

[SEAL]

Attest:

RUTH C. MASON
Attesting Officer

DONALD W. BANNER
Commissioner of Patents and Trademarks